(12) United States Patent
Zhang et al.

(10) Patent No.: US 7,732,458 B2
(45) Date of Patent: Jun. 8, 2010

(54) METHODS FOR PREPARING DEHYDROCAVIDINE, DEHYDROAPOCAVIDINE OR THEIR COMPOSITION, THEIR USE AND MEDICINAL COMPOSITION CONTAINING THEM

(75) Inventors: Weidong Zhang, Shanghai (CN); Hanxiong Li, Yunfeng Yunjing Garden, Toughe Rd. Baiyun District, Guangzhou (CN) 510515; Huiliang Li, Shanghai (CN); Chuan Zhang, Shanghai (CN); Runhui Liu, Shanghai (CN); Juan Su, Shanghai (CN); Xike Xu, Shanghai (CN)

(73) Assignee: Hanxiong Li, Guangzhou (CN)

( * ) Notice: Subject to any disclaimer, the term of this patent is extended or adjusted under 35 U.S.C. 154(b) by 0 days.

(21) Appl. No.: 11/806,874

(22) Filed: Jun. 5, 2007

(65) Prior Publication Data

US 2007/0249650 A1 Oct. 25, 2007

Related U.S. Application Data

(63) Continuation of application No. PCT/CN2005/001755, filed on Oct. 24, 2005.

(30) Foreign Application Priority Data

Dec. 29, 2004 (CN) .................. 2004 1 0099269

(51) Int. Cl.
*A61K 31/4738* (2006.01)
*C07D 491/02* (2006.01)

(52) U.S. Cl. ....................... 514/280; 546/48

(58) Field of Classification Search ................. 514/280; 546/48
See application file for complete search history.

(56) References Cited

FOREIGN PATENT DOCUMENTS

CN 200410099269.6 * 12/2004
WO WO 2006/069512 A1 * 7/2006

OTHER PUBLICATIONS

Bhakuni, D.S. et al.: The alkaloids of Corydalis Meifolia. J. of Natural Products, vol. 46, pp. 320-324, 1983.*
Li Hui-Liang et al.: Bioavailability and pharmacokinetics of four active alkaloids of traditional chinese medicine Yanhuanglian in rats following intravenous and oral administration. J. of Pharmaceutical & Biomed. Anal. vol. 41, pp. 1342-1346, 2006.*

* cited by examiner

*Primary Examiner*—Charanjit S Aulakh
(74) *Attorney, Agent, or Firm*—IPFortune LLC; Ruay L. Ho

(57) ABSTRACT

A method for preparing dehydrocavidine, dehydroapocavidine and their respective composition is provided. The composition is first prepared by isolating and purifying the quaternary ammonium alkaloid components from the medicinal plant "Yan Huang Lian" (*Corydalis saxicola* Bunting) through the processes of solvent extraction, water-phase organic extraction, crystallization and recrystallization, and then drying to obtain said composition containing dehydrocavidine and dehydroapocavine. When necessary, the composition or their crude extracts can be separated by chromatography to obtain dehydrocavidine or dehydroapocavidine. Dehydrocavidine, dehydroapocavidine or their respective composition can be used in manufacturing medicines for treating viral hepatitis, hepatic injury, influenza, AIDS, tumors or arrhythmia.

25 Claims, 2 Drawing Sheets

METHODS FOR PREPARING DEHYDROCAVIDINE, DEHYDROAPOCAVIDINE OR THEIR COMPOSITION, THEIR USE AND MEDICINAL COMPOSITION CONTAINING THEM

FIELD OF THE INVENTION

The present invention discloses a method for preparing dehydrocavidine (FIG. 1), dehydroapocavidine and their respective composition, comprising the following steps: isolating and purifying the quaternary ammonium alkaloid components from the medicinal plant "Yan Huang Lian" (*Corydalis saxicola* Bunting) through the processes of solvent extraction, water-phase organic extraction, crystallization and recrystallization, and then drying to obtain said composition containing dehydrocavidine and dehydroapocavine. When necessary, said composition or their crude extracts obtained from said steps can be separated by chromatography to obtain dehydrocavidine or dehydroapocavidine. Dehydrocavidine, dehydroapocavidine or their respective composition can be used in manufacturing medicines for treating viral hepatitis, hepatic injury, influenza, AIDS, tumors or arrhythmia.

The present invention relates to the fields of medicine and pharmacology, in particular, to a method of extracting dehydrocavidine, dehydroapocavidine, and their respective composition from a medicinal plant of Yan Huang Lian (*Corydalis saxicola* Bunting), and their pharmaceutical use.

BACKGROUND OF THE INVENTION

Hepatitis is one of the most harmful infectious diseases in the world, and is also related closely to the onset of liver cancer. According to statistical data from the World Health Organization (WHO), presently there are 350 million chronic hepatitis sufferers or asymptomatic patients infected by hepatitis viruses all over the world. All of these chronic hepatitis patients are at high risk of developing hepatocirrhosis and liver cancer. Over one million people die of diseases related to hepatitis, hepatocirrhosis and liver cancer each year. The incidence of hepatitis cases in China is high, and data shows that 90 percent of liver cancer patients were infected by the hepatitis viruses. Currently liver cancer is the second-most fatal tumor disease. To prevent and treat such a common, frequently occurring and refractory disease, researchers inside and outside of China have been focusing on and conducting clinical and pharmacological studies in liver protection and detoxification. Most countries treat chronic hepatitis B with a-interferon whose main effect is immunoregulation. Presently there are no specific drugs that can effectively treat hepatitis B and C caused by their respective viruses. The drugs against hepatitis B viruses are mostly the anti-HIV reverse transcriptase inhibitors and anti-herpes viruses DNA polymerase inhibitors. These two types of virus enzyme inhibitors are the target of anti-hepatitis B virus. The drugs used to fight hepatitis C viruses are mostly the broad-spectrum anti-virus drugs or RNA-virus inhibitors, and the immunoregulators having the activity of anti-viruses. However, the general problem with drugs currently available to use against hepatitis is that they are subject to drug-resistance.

Yan Huang Lian (*Corydalis saxicola* Bunting [*Corydalis thalictrifolia* Franch. Non Jameson ex Regel]), is a whole plant belonging to the family of papaveraceae. It is also known as Yan Hu (Guizhou), Yan Lian (Sichuan, Yunnan), Ju Hua Huang or Tu Huang Lian (Guangxi). Native residents in Guangxi use the roots of the plant as a pain killer, for detumescence, for drawing out pus and for treatment of scabies and swelling. Its current clinical application includes the use of its alkaloid extracts to treat hepatitis and hepatocirrhosis (Editorial Board of China Herbal. 1999. State Administration of Traditional Chinese Medicine. China Herbal, Vol. 3. Shanghai Science and Technology Press: Shanghai; 638-640).

In 1982, Chongyang Chen et al (Chen C Y, 1982. Pharmacological study of dehydrocavidine, the major constituent in Yan Huang-lian (*Corydalis, saxicola* Bunting). Trad Chin Med 7: 31-34.) investigated the pharmacological activity of dehydrocavidine which is the main constituent in *Corydalis saxicola* Bunting, and the results indicated that dehydrocavidine had sedative effects on the central nervous system; antispasm effects on the smooth muscles of the intestines; antibacterial effect in vitro; no effects on the blood sugar levels in normal mice; and effect on increasing the production of glycogen in vivo. In 1984, Qili Ye (Ye Q L. 1984. Anti-bacterial effect of dehydrocavidine from *Corydalis saxicola*. Gaungxi Zhongyiyao 3: 48-49.) investigated the anti-bacteria activity of dehydrocavidine in vitro, and the experiment proved that the dehydrocavidine had certain inhibitory effect on grampositive bacterium. In 1996, Peishan Xie, et al. (Xie Peishan et al, "Screening tests of Chinese traditional medicines or herbal medicines in antitumor activity." Shizhen Journal of Traditional Chinese Medicine Research, Vol. 7, no. 1, 1996, pages 19-20), reported that their anti-tumor experiment with this herb proved that the total alkali of *Corydalis saxicola* Bunting had a 30 percent inhibition rate on S180 carunclesarcoma at the dose of 1.6 mg/kg. In the past 10 years, some studies have indicated that the total alkali of *Corydalis saxicola* Bunting had an enhanced effect on the immune functions of mice, and certain inhibitory effects on the metabolism of DA and 5-HT in the rat's brain.

Yan Huang Lian (*Corydalis saxicola* Bunting) is clinically used as a supplementary therapeutic treatment of hepatitis. A study conducted by Zhongxuan Ren (Zhongxuan Ren, the efficacy analysis of 33 hepatitis cases treated with Yan Huang Lian (*Corydalis saxicola* Bunting), Clinical Focus, 18 (2): 94-95, 2003) showed that the injection of Yan Huang Lian (*Corydalis saxicola* Bunting Injecta) could effectively improve the clinical symptom of acute and chronic hepatitis. The Yan Huang Lian Injection combined with Shengmai injection have a distinct curative effect on hepatocirrhosis. Yan Huang Lian Injection combined with Danshen injection can effectively improve liver function, and relieve and inhibit liver fibrosis.

Although *Corydalis saxicola* Bunting has good clinical effects, the active constituents of this plant are still unclear and there are no practically feasible quality standards because of the lack of in-depth research on chemical constituents and the lack of sufficient screening of pharmacological activities.

SUMMARY

To overcome the shortcoming of the current art and solve the technical problems mentioned above, the present invention is to extract potent active constituents from Yan Huang Lian (*Corydalis saxicola* Bunting), a Chinese traditional medicinal plant, and is to screen out from these natural products the lead compounds with anti-hepatitis activities, and then screen out more active single compound from a series of derivative compounds through modification of chemical structure and synthesis of the lead compounds, and by combining with the study on relationship between structure and efficacy of anti-hepatitis B virus activities, the invention is to eventually lead to the discovery of drugs with promising clinical applications.

A plentiful quaternary ammonium alkali species and tertiary ammonium alkali species alkaloids that exist in Yan Huang Lian (*Corydalis saxicola* Bunting) are discovered by a systematic phytochemical separation, purification and structural identification of chemical constituents in this plant. Further screening of the pharmacological activity has proved that there are mainly dehydrocavidine and dehydroapocavidine in the quaternary ammonium alkali species and they are the active constituents against hepatitis, hepatitis B virus, tumor and arrhythmia.

FIG. 1 and FIG. 2 show the structural formula of dehydrocavidine and dehydroapocavidine. According to the chemical properties and solubility of dehydrocavidine and dehydroapocavidine, dehydrocavidine-dehydroapocavidine composition and their respective compounds are prepared by the methods of solvent extraction, water-phase organic extraction, crystallization purification, combined with the method of chromatography without employment of the traditional acid-base organic-solvent extraction. FIG. 1 and FIG. 2 show the structural formula of dehydrocavidine and dehydroapocavidine. According to the chemical properties and solubility of dehydrocavidine and dehydroapocavidine, dehydrocavidine-dehydroapocavidine composition and their respective compounds are prepared by the methods of solvent extraction, water-phase organic extraction, crystallization purification, combined with the method of chromatography without employment of the traditional acid-base organic-solvent extraction.

A method proposed in the present invention for preparing a dehydrocavidine-dehydroapocavidine composition, and their respective individual compounds comprises the following steps: isolate and purify the quaternary ammonium components from medicinal material of Yan Hung Lian (*Corydalis saxicola* Bunting) via solvent extraction, water-phase organic extraction, crystallization and recrystallization, and then dry to obtain the dehydrocavidine and dehydroapocavidine compositions which can be further separated by chromatography to obtain individual compounds of dehydrocavidine and dehydroapocavidine.

Said medicinal material of Yan Huang Lian (*Corydalis saxicola* Bunting) may be freshly collected raw medicinal material or commercially available medicinal material. The content of dehydrocavidine within the medicinal material should reach a certain level, and it provides that only the medicinal material with dehydrocavidine content above 0.5 percent can be used as the preparation material; if the dehydrocavidine content is too low, the yield rate of the products can not be guaranteed.

When using said solvent extraction, the solvents can be organic solvents such as water, acidic water, methanol, ethanol, propanol, butanol and ethyl acetate, or their mixture; the extraction methods can be ultrasonic extraction, percolation extraction or reflux extraction; the extraction can be repeated more than one time.

When using said water-phase organic extraction, the extracts of medicinal materials of Yan Huang Lian (*Corydalis saxicola* Bunting) can be dispersed in water, defatted with petroleum ether and extracted with appropriate organic solvents in order to remove the non quaternary ammonium alkali species. The organic solvents may be chloroform, dichloromethane, ether, ethyl acetate, butanol, etc. for this extraction. The extraction may also proceed directly with above solvents without defatting with petroleum ether. The extraction may be repeated more than one time.

When using the methods of crystallization, the extraction residues obtained from the water-phase extraction preparation are crystallized with an appropriate solvent in order to remove the inorganic salts and fractional non-quaternary ammonium alkali species. The crystallization solvents may be water, methanol, ethanol, butanol, acetone, etc., and the mixed solvent of two or more above solvents. The solvent can be used at a low temperature, room temperature or slightly heated.

When using the methods of recrystallization, the crude quaternary ammonium alkali species of Yan Huang Lian (*Corydalis saxicola* Bunting) obtained from the crystallization are dissolved by heating with appropriate solvents, and are filtrated and concentrated, then the solution is placed at a low temperature and the dehydrocavidine-dehydroapocavidine composition can be separated out from the solution. The solvents may be used individually or in a mixture of the following: methanol, ethanol, water, acidic water, acidic methanol, acidic ethanol. The acid used may be hydrochloric acid, sulfuric acid, phosphoric acid, nitric acid, perchloric acid, succinic acid, oxalic acid, formic acid, acetic acid or their mixture. The crystallization can be repeated more than once.

The drying method of said dehydrocavidine-dehydroapocavidine composition is atmospheric pressure drying or decompression drying, and may also be spray drying or freeze drying. The contents of dehydrocavidine and dehydroapocavidine are in the range of 5% to 99.5% (w/w) of the composition obtained from said methods.

Chromatography is used to obtain individual compounds of dehydrocavidine and dehydroapocavidine by separating the dehydrocavidine-dehydroapocavidine composition and crude extracts obtained from each step of the composition preparation. The chromatographic packing can be used individually or a combination of silica gel, aluminum oxide, polyamide, sephadex gel. The chromatography can be a column or a thin layer.

Experiments have demonstrated that the dehydrocavidine-dehydroapocavidine composition and their respective individual compounds have anti-hepatitis B virus activity and a protective effect on liver injury, and that they can promote the detoxification function of the liver, and also can protect the liver against chemical poisons. Their potency is superior to that of matrine.

The experiments have also demonstrated that the dehydrocavidine-dehydroapocavidine composition and their respective compounds have an inhibitory effect on the human telomerase, inhibit tumor growth, inhibit virus activity and inhibit arrhythmia.

The pharmaceutical composition for clinical therapy can be manufactured by using the dehydrocavidine-dehydroapocavidine composition and their individual compounds with the addition of one or more pharmaceutically acceptable excipients, which can be used to treat acute and chronic virus hepatitis, liver injury, influenza, tumors, AIDS and arrhythmia.

The pharmaceutically acceptable excipients are the regular excipients routinely used in pharmaceutical industry, for example, diluent, vehiculum such as water; filler material such as starch, sucrose; binder such as cellulose derivatives, alginate, glutin and polyvinylpyrrolidone; lubricators such as glycerin; disintegrants such as agar, calcium carbonate, sodium bicarbonate; absorption accelerators such as quaternary ammonium compounds; surfactants such as cetanol; adsorption matrices such as kaoline, bentonite; malactics such as tarcum powder, calcium and magnesium stearate, polyethylenepolythene. In addition, other supporting agents such as fragrances and sweetening agents can also be added.

The compounds can be administrated to the patients through oral administration, nasal inhalation, rectum or external rectum administration. For oral administration, the compounds can be prepared into solid preparations such as a tablet, powder, granules, capsules, and in liquid preparations such as water or oil-suspending agents or other liquid preparations such as syrups, elixirs; for external rectum administration, the compounds can be prepared into injection solution, water or oleo-suspending agents. The optimum preparations are tablet, coated tablet, capsule, suppository, nasal pressurized spray and injection solution.

All kinds of preparations of the pharmaceutical composition can be prepared by the methods routinely used in the field of pharmacology. For example, the active constituents can be combined with one or more excipients and then prepared to the desired preparations.

Employment of the method disclosed in the present invention can greatly increase the yield rate and transfer rate. The dehydrocavidine-dehydroapocavidine composition and their respective individual compounds prepared in said method have high content of quaternary ammonium alkaloids and a relatively stable ratio of the active constituents. They can be used for manufacturing pharmaceutical medicines to fight hepatitis, viruses, tumors and arrhythmia.

Examples of practices below are provided to help professionals in this field understand the invention, but are by no means intended to limit the scope of the present invention.

DETAILED DESCRIPTION OF THE INVENTION

Preferred Embodiment 1

Figure 1:
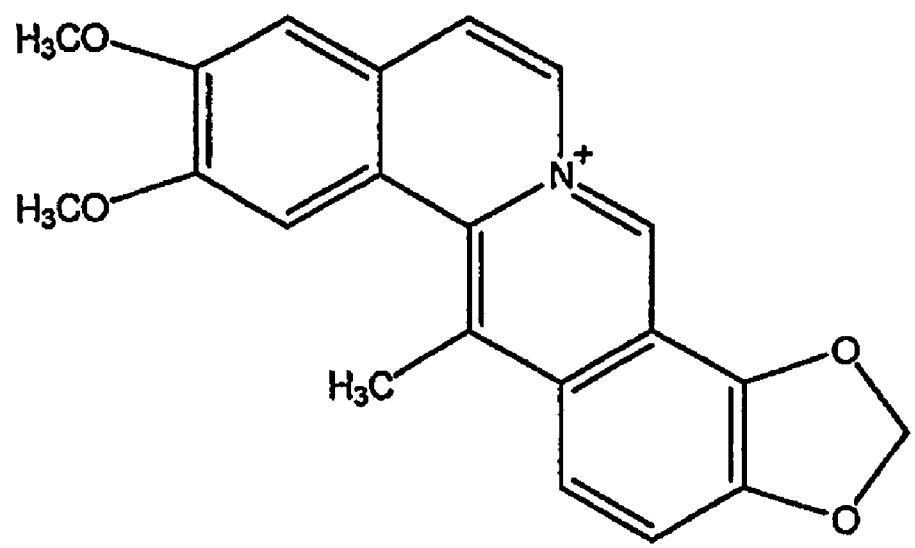
FIG. 1 is the structural formula of dehydrocavidine.
Figure 2:
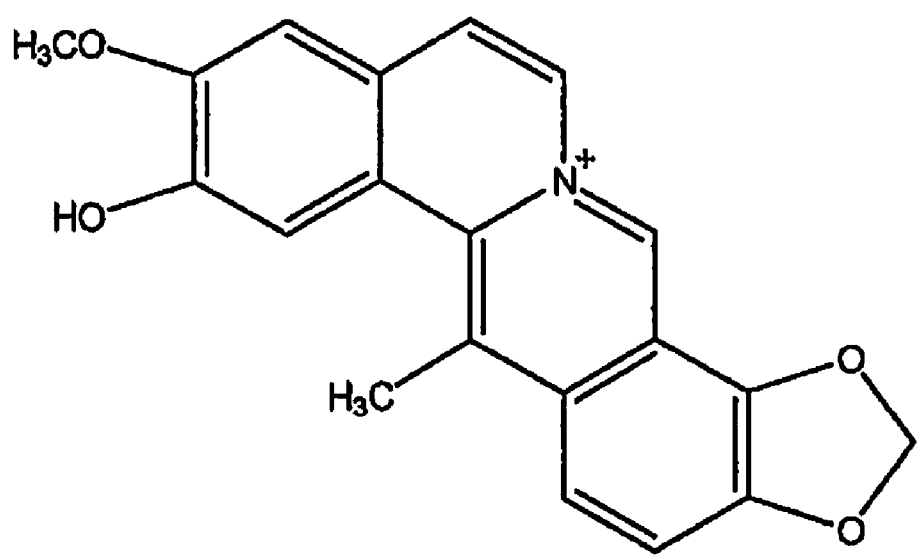
FIG. 2 is the structural formula of dehydroapocavidine.
Figure 3:
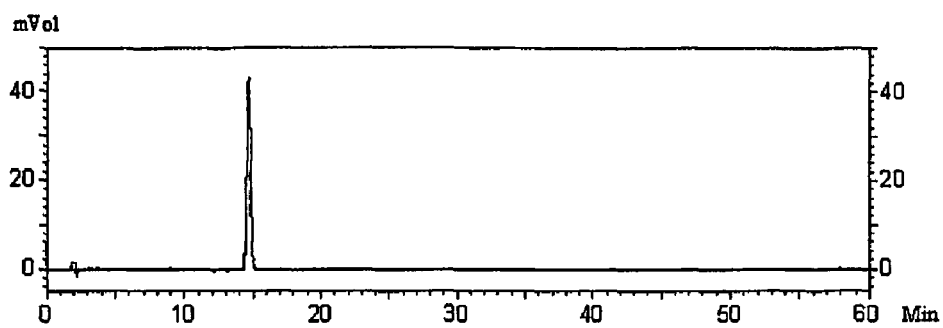
FIG. 3 is the HPLC chromatogram of standard dehydrocavidine.
Figure 4:
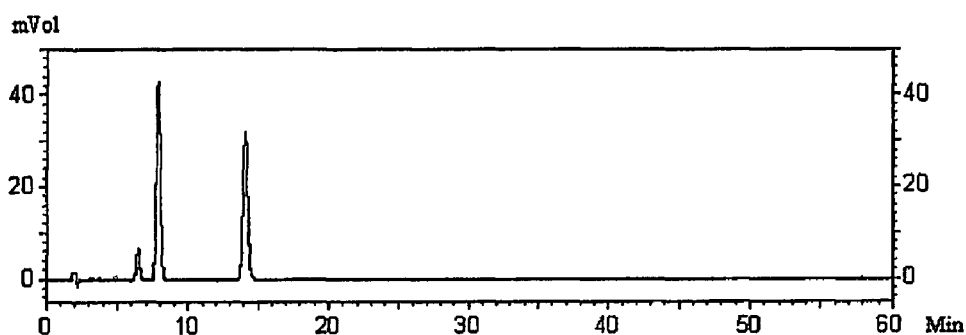
FIG. 4 is the HPLC chromatogram of dehydrocavidine-dehydroapocavidine composition.

2.5 kg of the dried medicinal plant Yan Huang Lian (*Corydalis saxicola* Bunting) are reflux extracted twice (2 hour one time) in 50 liters of 90 percent ethanol, and the extractive solution combined is concentrated to 580 g extracts. The extracts are dissolved in 2 liters of water, defatted by three times of extraction in 6 liter petroleum ether followed by three times of extractive purification in 6 liter chloroform. The extractive residues are gauze filtered to remove the solution and then are respectively washed by 2 liters of water and 2 liters of ethanol, and 62 g of crude extract are obtained after being filtered through gauze. The crude extract is dissolved in 1 liter of 1 percent hydrochloric acid ethanol solution, and hot filtration is performed. The filtrate is placed in a refrigerator at 4° C. overnight, and consequently, the dehydrocavidine-dehydroapocavidine composition crystals are separated out. 36 g of purified composition is obtained after being filtered and dried. The chromatogram of HPLC is shown in FIG. 4. Standards of dehydrocavidine are shown in FIG. 3.

Figure 5:
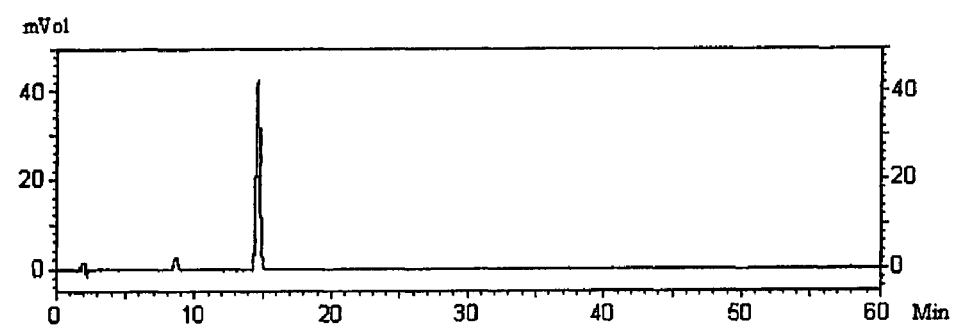
FIG. 5 is the HPLC chromatogram of dehydrocavidine compound.
Figure 6:
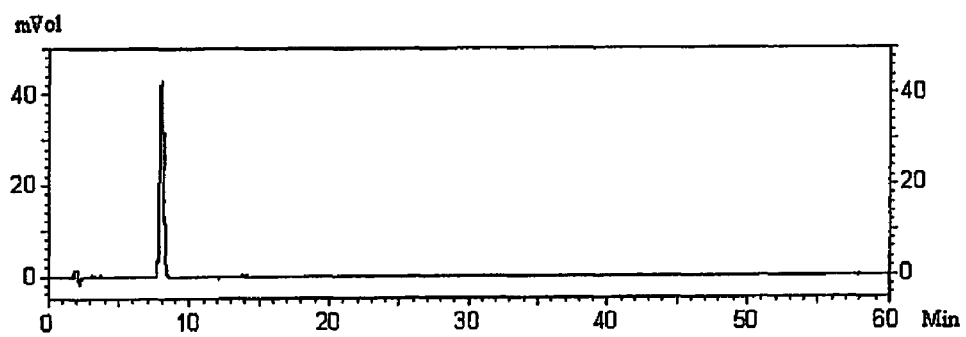
FIG. 6 is the HPLC chromatogram of the self-prepared dehydroapocavidine compound.

10 g of the dehydrocavidine-dehydroapocavidine composition is mixed with 50 g silica gel, and is then added to the top of a silica column, and a gradient elution is performed with a solvent system of chloroform:methanol (15:1~5:1) accompanied by TLC tracking. The eluate containing dehydrocavidine is combined and then concentrated by decompression to dry, resulting in a 3.9 g dehydrocavidine compound and a 3.7 g dehydroapocavidine compound respectively. The chromatograms of HPLC are showed in FIGS. 5 and 6.

Preferred Embodiment 2

Measuring the Content of Dehydrocavidine in the Medicinal Plant Yan Huang Lian (*Corydalis saxicola* Bunting)

Measuring the content of dehydrocavidine in the medicinal plant Yan Huang Lian (*Corydalis saxicola* Bunting) is performed by high performance liquid chromatography as shown in the Pharmacopoeia of China, and the methods and its chromatographic conditions are as follows:

Chromatographic conditions and the system applicability test: the packing material is octadecyl silane bonded silica gel (pls double check this term translated) and the mobile phase is A. Phosphoric acid saline buffer solution (each liter contains 20 mmol $KH_2PO_4$, 10 mmol triethylamine and 0.2% of phosphoric acid; B. ethyl nitrile. Employing A:B (78:22) as the mobile phase, the column temperature is at 30° C., the wavelength is 347 nm, and the flow rate is 0.8 ml/min and the sample collection time is 30 min. The value of the height equivalent to a theoretical plate related to dehydrocavidine should not be lower than 3000.

Preparation of the solvent for a standard sample: weigh precisely 10 mg of the standard sample of dehydrocavidine and place in a 100 ml measuring beaker; then add the mobile phase A:B (78:22) into the beaker up to the planned scale and shake well and save it as stock solution.

Measure precisely 5.0 ml of said stock solution and place it in a 25 ml measuring beaker, and then add the mobile phase (A:B=78:22) up to the planned scale and shake well. It can then be prepared as a solvent of 20 μg in 1 ml.

Preparation of solvent for test sample: grind the medicinal plant Yan Huang Lian (*Corydalis saxicola* Bunting) and sift it out with #20 sieve (0.850 mm screen aperture). Obtain 100 mg powder and weigh precisely, then place it in a 50 ml measuring beaker. The mobile phase (A:B=78:22) is added into the beaker up to the planned scale and is then ultrasonically treated for 30 minutes. It is then filtered out with micropore filtering membrane. The filtrate is obtained as the test sample.

Method for measurement: precisely 10 μl standard sample and test sample are pipetted out respectively and are loaded onto liquid chromatography. The content can be measured with the external standard method by calculating the peak area.

The results of the measurement of fresh and commercially available medicinal plant Yan Huang Lian (*Corydalis saxicola* Bunting) in accordance with said standards are shown in the following table:

| Code | Sources | Dehydrocavidine (%) |
|---|---|---|
| 1 | Collected at Hechi, Guangxi - 1 | 0.80 |
| 2 | Collected at Hechi, Guangxi - 2 | 0.72 |
| 3 | Collected at Hechi, Guangxi - 3 | 0.76 |
| 4 | Purchased at the medicinal market of Haozhou, Anhui | 0.68 |
| 5 | Purchased at the medicineal market of Anguo, Hebei | 0.72 |

According to the results of the above measurements, the limit for dehydrocavidine content should not be set below 0.5 percent. Only medicinal materials that meet this standard can be used.

Preferred Embodiment 3

2.5 kg fresh medicinal plant of Yan Huang Lian (*Corydalis saxicola* Bunting) are ultrasonically extracted twice for 1 hour at a time, and the extractive solution combined is concentrated by decompression to 415 g extracts. The extracts are dissolved in 2 liters of water, and purified by extracting it three times in 6 liters of dichloromethane. The extractive residues are gauze filtered to remove the solution and are then washed with 2 liters of ethanol, and 53 g of crude extract are obtained after being filtered through gauze. The crude extract obtained is dissolved in 1 liter of 2.5 percent hot acetic acid solution, and hot filtration is performed. The filtrate is placed in a refrigerator to cool overnight, and the dehydrocavidine-dehydroapocavidine composition is then separated out. 27 g of purified composition is obtained after being paper filtered and freeze dried. The content of the dehydrocavidine-dehydroapocavidine composition is measured and the result shows 17 percent of dehydrocavidine and dehydroapocavidine in the composition.

10 g of the dehydrocavidine-dehydroapocavidine composition obtained from the above step is mixed with 40 g of the aluminum oxide, and are then added to the top of an aluminum oxide column, and a gradient elution is employed with a solvent system of petroleum ether: ethyl acetate (1:8~1:15) accompanied by TLC tracking. The eluate containing dehydrocavidine is combined and then is concentrated by decompression to constant weight, resulting in a 1.3 g dehydrocavidine compound and a 1.9 g dehydroapocavidine compound respectively.

Preferred Embodiment 4

2.5 kg of commercially available medicinal plant of Yan Huang Lian (*Corydalis saxicola* Bunting) are percolationally extracted in 50 liter ethyl acetate, and the percolative solution collected is concentrated by decompression to 475 g extracts. The extracts are dissolved in 2 liters of water, and defatted three times through extraction in 6 liters of petroleum ether, and are then purified three times through extraction in 6 liters of ethyl acetate. The extractive residues are gauze filtered to remove the solution and are then washed respectively by 2 liters of ethanol and 2 liters of acetone. 63 g of crude extract are obtained after being filtered through gauze. The crude extracts obtained are dissolved in 1 liter of 1 percent hot sulfuric acid methanol solution, and hot filtration is performed. The filtrate is placed in a refrigerator to cool overnight, and the dehydrocavidine-dehydroapocavidine composition is subsequently separated out. 29 g of purified composition is obtained after being paper filtered and decompression dried to a constant weight.

The content of the dehydrocavidine-dehydroapocavidine composition is measured and the result shows 99.5 percent of dehydrocavidine and dehydroapocavidine in the composition.

5 g of the dehydrocavidine-dehydroapocavidine composition obtained from the above step is mixed with 20 g polyamide, and are then added to the top of a polyamide column, and a gradient elution is employed with a solvent system of methanol:water (4:1) accompanied by TLC tracking. The eluate containing dehydrocavidine is combined and is then concentrated by decompression to a constant weight, resulting in obtaining 0.9 g of a dehydrocavidine compound and 0.75 g of a dehydroapocavidine compound respectively.

Preferred Embodiment 5

2.5 kg fresh medicinal plant of Yan Huang Lian (*Corydalis saxicola* Bunting) are reflux extracted twice for 2 hours at a time in 25 liters of hot water, and the extractive solution is combined and is then concentrated by decompression to 2.5 liter extracts. The extracts are purified four times through extraction in 10 liters of butanol. The extractive residues are gauze filtered to remove the solution and are then washed with 2 liters of water. 31 g of crude extract are obtained after being filtered through gauze. The crude extract obtained is dissolved by heating in 0.5 liters of ethanol and hot filtration is performed. The filtrate is placed in a refrigerator to cool overnight, and the dehydrocavidine-dehydroapocavidine composition is subsequently separated out. 15 g of purified composition is obtained after being filtered with filter paper and decompression dried to a constant weight.

The content of the dehydrocavidine and dehydroapocavidine in the dehydrocavidine-dehydroapocavidine composition is measured and the result shows 5.01 percent of dehydrocavidine and dehydroapocavidine in the composition.

200 mg of the dehydrocavidine-dehydroapocavidine composition obtained from the above step is dissolved with 10 ml of methanol, and are then loaded to the top of the sephadex gel column, and a gradient elution is employed with 30%~70% methanol, accompanied by TLC tracking. The eluate containing dehydrocavidine is combined and is then concentrated by decompression to a constant weight, resulting in obtaining 22 mg of a dehydrocavidine compound and 14 mg of a dehydroapocavidine compound respectively.

Preferred Embodiment 6

0.5 kg of commercially available dried medicinal plant of Yan Huang Lian (*Corydalis saxicola* Bunting) are refluxly extracted twice for 1 hour at a time in 5 liters of propanol, and the extractive solution is combined and is then concentrated by decompression to 105 g extracts. The extracts are mixed with 150 g of silica gel and are loaded to the top of the silica gel column, and a gradient elution is employed with a solvent system of chloroform: methanol, accompanied by TLC tracking. The eluate with the same spot containing dehydrocavidine is combined and is then concentrated by decompression to a constant weight, resulting in obtaining 1.9 g dehydrocavidine compound and a 1.4 g dehydroapocavidine compound respectively.

Preferred Embodiment 7

0.5 kg of fresh medicinal plant of Yan Huang Lian (*Corydalis saxicola* Bunting) are extracted through percolation in 10 liters of a 1 percent hydrochloric acid solution, and the extractive solution is collected and is then concentrated by decompression to 95 g extracts. The extracts are dissolved in 1 liter of water, and are then purified three times through extraction in 3 liters of dichloromethane. The extractive residues are gauze filtered to remove the solution. 47 g of extracts are obtained after being filtered through gauze and dried by decompression. The extracts are mixed with 100 g of polyamide and are loaded to the top of the polyamide column, and a gradient elution is employed with a solvent system of ethanol:water (1:10~1:1), accompanied by TLC tracking. The eluate of the same band containing dehydrocavidine is combined and is then concentrated to a constant weight, resulting in obtaining 2.3 g of a dehydrocavidine compound and 1.8 g of a dehydroapocavidine compound respectively.

Preferred Embodiment 8

1 kg of fresh medicinal plant Yan Huang Lian (*Corydalis saxicola* Bunting) are ultrasonically extracted twice for two hours at a time in 20 liters of butanol, and the extractive solution is combined and is then concentrated by decompression to 156 g extracts. The extracts are dissolved in 1.5 liters of water, and defatted by extraction four times in 6 liters of petroleum ether, and are then purified by extraction four times in 6 liters of ethyl acetate. The extractive residues are gauze filtered to remove the solution and are then washed respectively in 2 liters of ethanol and 2 liters of acetone. 63 g of extracts are obtained after being filtered through gauze and dried by decompression. 200 mg of the extract is dissolved in 10 ml of methanol and is then loaded to the top of the sephadex gel column. A gradient elution is used with methanol, accompanied by TLC tracking. The eluate in the same band containing dehydrocavidine is combined and is then concentrated by decompression to a constant weight, resulting in obtaining 23 mg of a dehydrocavidine compound and 15 mg of a dehydroapocavidine compound respectively.

Preferred Embodiment 9

1 kg of commercially available dried medicinal plant Yan Huang Lian (*Corydalis saxicola* Bunting) are extracted by reflux two times, each for one hour at a time in 10 liters of 70 percent methanol, and the extractive solution is collected and is then concentrated by decompression to 1 liter of extracts. The extracts are purified by extracting them three times in 3 liters of chloroform. The extractive residues are gauze filtered to remove the solution and are then washed with 1 liter of ethanol. 23 g of crude extract are obtained after being filtered through gauze. 50 mg of the crude extracts is dissolved in 2 ml methanol and 0.5 ml sample from the dissolved extracts is loaded to the sheet with a thin layer of silica gel. A developing solvent of ethyl acetate:methanol:isopropanol:ammonia (30:15:15:7.5:1.5) is employed and the sample is developed in the chromatographic chamber. The gel with corresponding bands to dehydrocavidine and dehydroapocavidine is peeled off from the sheet and transferred into a flask, which is then ultrasonically extracted in an appropriate amount of methanol. The extracts obtained are filtered and concentrated by decompression to dry. 11 mg and 7 mg of individual compounds of dehydrocavidine and dehydroapocavidine are obtained respectively.

Preferred Embodiment 10

| Tablet: | Active constituents | 10 mg |
|---|---|---|
| | Lactose | 187 mg |
| | Cornstarch | 50 mg |
| | Magnesium stearate | 3 mg |

Preparation: the mixture of active constituents, lactose and cornstarch is wetted with water. The wetted mixture is then sifted out and dried. The dried mixture is sifted out again. Then the mixture is compressed to tablets (250 mg/tablet) after adding magnesium stearate. The content of active constituents is 10 mg per tablet.

Preferred Embodiment 11

| Intravenous drip: | Active constituents | 2 mg |
|---|---|---|
| | Sodium chloride | 9 mg |

Preparation: the active constituents and sodium chloride are dissolved in appropriate amount of fluid for injection. The solution is filled in a container in aseptic condition after being filtered.

Preferred Embodiment 12

The Inhibitory Effects of Dehydrocavidine-Dehydroapocavidine Composition and their Respective Compounds on Hepatitis Viruses The inhibitory effects of said dehydrocavidine-dehydroapocavidine composition and their respective compounds on hepatitis B viruses are determined using the cell line 2.2.15 of human liver cancer cell (Hep G2) transfected by hepatitis B virus DNA. The results are showed in Table 1.

TABLE 1

The toxicity of dehydrocavidine-dehydroapocavidine composition
and their respective compounds to cell Hep G2 2.2.15 and their
inhibitory effects on HBeAg, HBsAg

| Samples | Concentration (μmol/ml) | Toxicity to cell | Inhibition frequency to HBeAg (%) | Inhibition frequency to HBsAg (%) |
|---|---|---|---|---|
| dehydrocavidine | 0.4 | − | 57.2 | 34.6 |
|  | 0.2 | − | 21.6 | 31.4 |
|  | 0.1 | − | 20.5 | 28.4 |
| dehydroapocavidine | 0.4 | − | 62.1 | 28.6 |
|  | 0.2 | − | 33.5 | 21.3 |
|  | 0.1 | − | 26.5 | 15.7 |
| composition | 0.4 | + | / | / |
|  | 0.2 | − | 50.1 | 32.3 |
|  | 0.1 | − | 44.1 | 19.6 |
| 3TC | 1.0 | − | 24.5 | 4.8 |

−: "no obvious toxicity" means cell livability ≧75% using MTT method;
+: "showing toxicity" means cell livability ≦75%.

Preferred Embodiment 13

The Animal Verification on Protective Effects of Dehydrocavidine-Dehydroapocavidine Composition and their Respective Compounds on Experimental Liver Injury The model of acute liver injury induced by thioacetamide in mice Experimental animals: Kunming mice, male or female, weighing 19-22 g, are used in the study. Animals are housed in an animal room with a natural photoperiod and room temperature (23±2° C.), and maintained with free access to standard rodent pellet food and water ad libitum.

1.2 Experimental methods: All mice are randomly divided to 7 groups. All the other groups are treated with 30 mg/kg thioacetamide to induce acute liver injury model except the normal control group. Then all groups are successively dosed three times at an interval of 3 hours, 6 hours and 9 hours after being infected, and the blood samples were obtained at 24 hours (i.e. the next day) after the final dose. The follow markers and liver weight were measured and also the pathological examination were performed (Table 2).

TABLE 2

The effects of tested reagents on the markers of the model of acute liver injury
induced by thioacetamide in mice (X ± SD, n = 20)

| Groups | ALT | AST | Liver index (g liver wt./100 g body wt.) |
|---|---|---|---|
| Dehydrocavidine | 873.50 ± 251.82[††] | 237.10 ± 73.27[††] | 5.36 ± 0.54 |
| Dehydroapocavidine | 823.26 ± 178.42[††] | 241.13 ± 62.81[††] | 5.14 ± 0.48 |
| Composition | 924.72 ± 173.23 | 271.98 ± 123.82 | 4.93 ± 0.44 |
| Positive contrast | 885.30 ± 248.27[†] | 293.30 ± 175.27[†] | 4.69 ± 0.58 |
| NS saline | 1183.70 ± 238.53 | 366.10 ± 71.42 | 4.65 ± 0.51 |
| Control | 701.30 ± 117.25 | 293.60 ± 62.75 | 4.78 ± 0.50 |

*compared with control group: [†]$p < 0.05$; [††]$p < 0.01$

Results: In contrast with the control group, the dehydrocavidine species chemicals can markedly relieve acute liver injury induced by thioacetamide in mice.

2. The Model of Acute Hepatic Toxicity Induced by Carbon Tetrachloride in Rats 2.1 Experimental Animals Matured SD rats, male or female, weighing 250-350 g are used in the study. Animals are maintained with free access to standard rodent pellet food and water ad libitum.

2.2 Experimental Methods

All rats are randomly divided into 6 groups. All the other groups are treated with 0.5 ml/100 g of 50 percent carbon tetrachloride by hypodermic injection to induce acute hepatic toxicity model, except the control group, and are dosed one time simultaneously. Then all groups will be successively dosed at 4 hours and 8 hours, and the blood samples obtained at 12 hours after the final dose for determining ALT and AST. The animals are killed to measure their liver weight and to perform a pathological examination (Table 3).

TABLE 3

The effects of tested reagents on certain markers of the model
of acute hepatic toxicity induced by carbon tetrachloride in rats
(X ± SD, n = 20)

| Groups | ALT | AST |
|---|---|---|
| Dehydrocavidine | 774.30 ± 217.11[††] | 1116.54 ± 348.27[††] |
| Dehydroapocavidine | 955.36 ± 327.18[††] | 903.52 ± 256.94[††] |
| Composition | 1083.22 ± 824.61[††] | 1083.12 ± 526.81[††] |
| NS saline | 4865.18 ± 212.33 | 4126.54 ± 245.37 |
| Positive contrast | 1435.27 ± 235.62 | 1382.23 ± 173.36 |
| Control | 926.73 ± 121.52 | 913.83 ± 139.77 |

*compared with negative control group: [†]$p < 0.05$; [††]$p < 0.01$

Results: In contrast with the negative control group, the dehydrocavidine species chemicals can markedly relieve the acute hepatic toxicity induced by carbon tetrachloride in rats.

3. The Model of Hepatic Toxicity Induced by D-Galactosamine in Rats 3.1 Experimental Animals Matured SD rats, male or female, weighing 250-350 g are used in study. Animals are maintained with free access to standard rodent pellet food and water ad libitum.

3.2 Experimental Methods

All rats are randomly divided into 4 groups. All groups except the control group are treated simultaneously with 800 mg/kg of 50 percent D-galactosamine by intraperitoneal injection to induce acute hepatic toxicity model. The blood samples are obtained 12 hours after the final dose for determining SGPT and TBIL. The animals are killed to measure their liver weight and to perform a pathological examination (Table 4).

TABLE 4

The effects of tested reagents on the model of acute hepatic toxicity induced by carbon tetrachloride in rats (X ± SD, n = 20)

| Groups | ALT | AST | Liver index (g liver wt./100 g body wt.) |
|---|---|---|---|
| Dehydrocavidine | 846.28 ± 172.54†† | 241.20 ± 65.53†† | 5.10 ± 0.36 |
| Dehydroapocavidine | 1027.10 ± 277.38 | 345.20 ± 68.29 | 4.47 ± 0.47 |
| Composition | 829.17 ± 103.42 | 338.21 ± 58.82 | 4.01 ± 0.25 |
| Positive contrast | 837.28 ± 172.63†† | 284.39 ± 171.92 | 4.72 ± 0.44 |
| NS saline | 1204.30 ± 219.78 | 383.27 ± 67.28 | 4.79 ± 0.51 |
| Control | 726.54 ± 103.36 | 228.18 ± 37.22 | 4.63 ± 0.32 |

*compared with control group: †$P < 0.05$; ††$P < 0.01$

4. The Model of Liver Fibrosis Induced by Carbon Tetrachloride in Rats 4.1 Experimental Animals Wistar male rats, weighing 100-150 g are used in the study. Animals are housed in an animal room with a 12 h: 12 h photoperiod and at 22° C. Animals are maintained with free access to standard rodent pellet food and water ad libitum 4.2 Experimental Methods All Wistar male rats are treated with 0.3 ml/(100 g body weight) of 40 percent carbon tetrachloride (dissolved in peanut oil) by hypodermic injection twice a week for 12 weeks to induce acute hepatic fibrosis model, all in phase IV. Then all rats in hepatic fibrosis are randomly divided into the following groups: normal saline (NS) group, sample group and positive contrast group. The NS group rats are treated with 0.2 ml normal saline by intramuscular injection for 8 weeks, and simultaneously, all the other groups are treated with samples one time a day for 8 weeks. The blood samples are obtained from the inferior vena cava 8 weeks later for determining biochemical markers. After that, all rats are killed, and the right lobes of the livers are fixed in neutral formaldehyde solution for histological examination. The results are shown in Table 5.

TABLE 5

The effects of tested reagents on the model of chronic hepatic toxicity induced by carbon tetrachloride in rats (X ± SD, n = 20)

| Groups | ALT | AST | Hydroxyprodine in Liver |
|---|---|---|---|
| Dehydrocavidine | 1113.4 ± 247.6 | 987.3 ± 237.9 | 0.162 ± 0.013 |
| Dehydroapocavidine | 973.2 ± 273.5 | 1057.1 ± 338.7 | 0.175 ± 0.018 |
| Composition | 1113.4 ± 247.6 | 987.3 ± 237.9 | 0.162 ± 0.013 |
| NS saline | 2284.2 ± 273.6 | 2949.9 ± 1572.4 | 0.195 ± 0.024 |
| Positive contrast | 1644.7 ± 158.3 | 1834.6 ± 836.4 | 0.217 ± 0.040 |
| Control | 989.6 ± 180.8 | 1085.3 ± 437.7 | 0.169 ± 0.018 |

*compared with negative control group: †$P < 0.05$; ††$P < 0.01$

Results: In contrast with the control group, the dehydrocavidine species chemicals can markedly relieve the chronic hepatic toxicity induced by carbon tetrachloride in rats.

Preferred Embodiment 14

The Inhibitory Effects of Dehydrocavidine-Dehydroapocavidine Composition and their Respective Compounds on Telomerase Activity The lead compounds with the inhibitory effect on telomerase activity are preliminary screened from the potent components of Chinese herbal medicine by a cell-free system. The telomerase proteins are extracted from tumor cells whose telomerase activity showed positive. The plant effective constituents' effects on telomerase activity are tested by the standard method of Telomeric Repeat Amplification Protocol (TRAP) which is the standard method for testing telomerase activity. All effective constituents (10-100 μmol) are incubated with the extracts from tumor cells for a specific amount of time (10-20 min), then TRAP testing is performed and the IC50 are calculated. The results are shown in Table 6.

TABLE 6

The inhibitory effects of dehydrocavidine species compounds on telomerase

| Groups | $IC_{50}$ (mmol) |
|---|---|
| dehydrocavidine | 17 |
| dehydroapocavidine | 10 |
| composition | 19 |

-: "no inhibition activity" means $IC_{50} \geq 100$ mmol by TRAP method.

Preferred Embodiment 15

The Inhibitory Effects of Dehydrocavidine-Dehydroapocavidine Composition and their Respective Compounds on HIV Viruses Tested Reagents Preparation of samples and solvents: the tested reagents are prepared in DMSO according to the planned concentration. Conservation: 4° C. AZT (zidouvding) serves as a positive control sample.

1.2 Cell and Virus

HIV-1 III B comes from the USA; MT4 cell line comes from Japan.

1.3 The Toxicity Experiments of Compounds on Cells

MT4 cells are cultured in 96-well plates (2×105 cells/ml, 0.1 ml/well) and the verifying compounds are added and compared against the positive control sample AZT, and the normal cell control group at the same time. Comparisons against DMSO control group and MT4 cell control group are also performed. The culture is maintained at 37° C., 5 percent CO2 for 6 days. The cell activities are tested by the MTT method to determine TC50.

1.4 The Inhibitory Effects of the Compounds on HIV-Induced MT4 Cell Pathological Effects To determine viral toxicity, HIV are diluted 10 fold in 8 serial [Chinese version is unclear, and this is an educated guess] and MT4 cell pathological effects are then observed in the culture solution of RPMI-1640. Calculated TCID50 is 10-6. The normal cell control group and virus control group are also performed. The samples with five concentrations per group that are diluted by 2 times and 100 μl AZT are added in cell or virus cultures. All concentrations of samples are performed in three repeated wells. The experiments are maintained at 37° C., 5 percent CO2 for 72 hours. Then the cell pathological effects (CPE) are observed under an inverted microscope. IC50 and selective index SI (TC50/IC50) are calculated in Table 7.

TABLE 7

The inhibitory effects of dehydrocavidine species compounds on HIV viruses

| Groups | $IC_{50}$ (μg/ml) | $TC_{50}$ (μg/ml) | SI |
|---|---|---|---|
| dehydrocavidine | 12.5 | >1000 | >80 |
| dehydroapocavidine | 6.25 | 250 | 40 |
| composition | 12.5 | 500 | 40 |
| AZT | 0.1 | 500 | 5000 |

Note:
$IC_{50}$ is 50 percent effective concentration;
$TC_{50}$ is 50 percent non-toxic concentration;
SI is the selective index;
—means no effect.

Results: The dehydrocavidine, dehydroapocavidine and their respective composition all have certain inhibitory effects on HIV viruses Preferred Embodiment 16

The Inhibitory Effects of Dehydrocavidine-Dehydroapocavidine Composition and their Respective Compounds on Influenza Viruses Tested Reagents Preparation of samples and solvents: the tested reagents are prepared in DMEM medium according to the planned concentration. Conservation: 4° C. Ribavirin served as the positive control reagent.

1.2 Cell and Virus

MDCK (Madin darby canin kidney) cell and influenza A1 virus are purchased from the Institute of Virology, Chinese Academy Preventive Medicine (Beijing, China).

1.3 Preparation of MDCK Cell Growth Medium, Cell Maintenance Medium, Versense Solution and Digestive Juice.

Prepared as shown in the cited literature (Guo Yuanji, Cheng Xiaowen, 1997).

2 Experimental Methods 2.1 MDCK Cells Subculture and Influenza Viruses Culture: Performed in Accordance with the Methods Shown in the Cited Literature by Guo Yuanji, Cheng Xiaowen, 1997.

2.2 Cell Toxicity

The sample (0.1 ml/well) is added on the cell plates that are covered with a layer of cells, subsequently, the cell maintenance medium is added in until the final volume 1 ml/well. The cells are maintained at 37° C., 5 percent CO2 for 72 hours. The cell pathological effects (CPE) are observed under an inverted microscope in contrast with the MDCK cell. All experiments are repeated 2 times. The results indicate that samples do not have nonspecific cell pathological effects (CPE) on MDCK cells.

2.3 Anti-Influenza Virus Experiment

MDCK cells are cultured in 96-well cell culture plates. A normal cell control group, a virus control group, a positive control group and a testing group are set up in the experiment. The influenza A1 viruses are added in the virus control group and the testing group at 37° C. for 2 hour absorption, and are then removed. The samples with different concentrations are respectively added in each group. The experiments are maintained at 37° C., 5 percent CO2 for 3 days. The result of the experiment is then observed and the different compounds of the 50 percent inhibitory concentration of IC50 on viruses are displayed in Table 8.

TABLE 8

The inhibitory effects of dehydrocavidine species compounds on influenza viruses

| Groups | $IC_{50}$ (mmol/L) |
|---|---|
| dehydrocavidine | 7.4 |
| dehydroapocavidine | 4.2 |
| Composition | 5.1 |
| Ribavirin | 3.2 |

Results: The dehydrocavidine, dehydroapocavidine and their composition all have markedly inhibitory effects on influenza viruses.

Preferred Embodiment 17

The Antagonistic Effects of Dehydrocavidine-Dehydroapocavidine Composition and their Respective Compounds on Arrhythmia The antagonistic effects of the dehydrocavidine species compounds on arrhythmia induced by aconitine Tested Samples The samples are dissolved in hot normal saline up to the needed concentration. Normal saline serves as the control solution. Propafenone serves as a positive control sample.

1.2 Experimental Methods:

Wistar rats of both sexes are randomly grouped and anesthetized by urethane (1.2 g/kg), II lead electrocardiogram is recorded. The groups are administered the following drugs by vena femoralis injection: (1) the compound (5 mg/kg, if possible 2.5 mg/kg), (2) propafenone (7 mg/kg), (3) control solution (2 mg/kg). After 5 minutes, aconitine solution (5 μg/ml) was delivered intravenously at a constant speed of 0.08 ml/min. The volume of aconitine solution is recorded when VP, VT and VF occur, and the electrocardiogram is also recorded. EV50 (VF) values are calculated by regression analysis on the basis of the dosage of aconitine consumed by VF in each experiment. The results are shown in Table 9.

TABLE 9

The $ED_{50}$ of the dehydrocavidine species compounds

| Groups | $ED_{50}$ ($10^{-6}$ mol/Kg) |
|---|---|
| dehydrocavidine | 7.33 |
| Dehydroapocavidine | 4.26 |
| Composition | 5.17 |

The phenomenon that the dosage of aconitine is increased and the emerging time of VT and (or) VF is postponed after the tested compounds are intravenously injected, indicate that dehydrocavidine, dehydroapocavidine and the dehydrocavidine-dehydroapocavidine composition all have certain preventive effects on arrhythmia induced by aconitine. The phenomenon that the dosage of aconitine is increased and the emerging time of VT and (or) VF is postponed after the tested compounds are intravenously injected, indicate that dehydrocavidine, dehydroapocavidine and the dehydrocavidine-dehydroapocavidine composition all have certain preventive effects on arrhythmia induced by aconitine.

What we claim is:

1. A method of preparing dehydrocavidine-dehydroapocavidine composition and their respective individual compounds comprises:
    isolating and purifying the quaternary ammonium alkaloid species from a medicinal plant of Yan Huang Lian (*Corydalis saxicola* Bounting) through solvent extraction, water-phase organic extraction, crystallization and recrystallization; and
    using drying methods to prepare and obtain dehydrocavidine-dehydroapocavine composition, the composition or the crude extracts obtained from said steps can be separated by chromatography to obtain individual compounds of dehydrocavidine and dehydroapocavidine.

2. The method as claimed in claim 1, wherein the solvents of said solvent extraction can be water, acidic water, methanol, ethanol, propanol, butanol and ethyl acetate, or a mixture of these solvents.

3. The method as claimed in claim 2, wherein the content of dehydrocavidine and dehydroapocavidine within the composition is in the range of 5% to 99.5% (w/w).

4. The method as claimed in claim 1, wherein said preparation method further comprises, in said solvent extraction, employing ultrasonic extracting, percolation extracting or reflux extracting.

5. The method as claimed in claim 4, wherein the content of dehydrocavidine and dehydroapocavidine within the composition is in the range of 5% to 99.5% (w/w).

6. The method as claimed in claim 1, wherein the extracts obtained in said water-phase extraction are dispersed in water, defatted with petroleum ether and extracted with appropriate organic solvents in order to remove the non-quaternary ammonium alkaloid species.

7. The method as claimed in claim 6, wherein the organic solvents used in said water-phase organic extraction can be chloroform, dichloromethane, ether, acetate ether, ethyl acetate, or butanol.

8. The method as claimed in claim 7, wherein the content of dehydrocavidine and dehydroapocavidine within the composition is in the range of 5% to 99.5% (w/w).

9. The method as claimed in claim 6, wherein the content of dehydrocavidine and dehydroapocavidine within the composition is in the range of 5% to 99.5% (w/w).

10. The method as claimed in claim 1, wherein the extracts obtained in said water-phase organic extraction are dispersed in water; and the non-quaternary ammonium alkaloid species can be removed directly with appropriate organic solvents.

11. The method as claimed in claim 10, wherein the organic solvents used in said water-phase organic extraction can be chloroform, dichloromethane, ether, acetate ether, ethyl acetate, or butanol.

12. The method as claimed in claim 11, wherein the content of dehydrocavidine and dehydroapocavidine within the composition is in the range of 5% to 99.5% (w/w).

13. The method as claimed in claim 10, wherein the content of dehydrocavidine and dehydroapocavidine within the composition is in the range of 5% to 99.5% (w/w).

14. The method as claimed in claim 1, wherein in the method of crystallization, the solvents can be water, methanol, ethanol, butanol, acetone, or their mixture.

15. The method as claimed in claim 14, wherein the content of dehydrocavidine and dehydroapocavidine within the composition is in the range of 5% to 99.5% (w/w).

16. The method as claimed in claim 1, wherein in said methods of recrystallization, the solvents used can be methanol, ethanol, water, acidic water, acidic methanol, acidic ethanol or their mixture.

17. The method as claimed in claim 16, wherein the content of dehydrocavidine and dehydroapocavidine within the composition is in the range of 5% to 99.5% (w/w).

18. The method as claimed in claim 1, wherein in said method of recrystallization, the acid used can be hydrochloric acid, sulfuric acid, phosphoric acid, nitric acid, perchloric acid, succinic acid, oxalic acid, acetic acid, formic acid, or their mixture.

19. The method as claimed in claim 18, wherein the content of dehydrocavidine and dehydroapocavidine within the composition is in the range of 5% to 99.5% (w/w).

20. The method as claimed in claim 1, wherein the drying method can be decompression drying, spray drying or freeze drying or their combination.

21. The method as claimed in claim 20, wherein the content of dehydrocavidine and dehydroapocavidine within the composition is in the range of 5% to 99.5% (w/w).

22. The method as claimed in claim 1, wherein filling materials for chromatography can be silica gel, aluminum oxide, polyamide, sephadex gel, or their mixture.

23. The method as claimed in claim 22, wherein the content of dehydrocavidine and dehydroapocavidine within the composition is in the range of 5% to 99.5% (w/w).

24. The method as claimed in claim 1, wherein the chromatography can be column or thin layer, or their combination.

25. The method as claimed in claim 24, wherein the content of dehydrocavidine and dehydroapocavidine within the composition is in the range of 5% to 99.5% (w/w).

* * * * *